United States Patent [19]

Brill, III

[11] 4,100,627

[45] Jul. 18, 1978

[54] LOW OILING GEL FILLED FLEXIBLE ARTICLES AND GELS THEREFOR

[75] Inventor: Alfred P. Brill, III, Laurinburg, N.C.

[73] Assignee: Dow Corning Corporation, Midland, Mich.

[21] Appl. No.: 755,322

[22] Filed: Dec. 29, 1976

Related U.S. Application Data

[63] Continuation-in-part of Ser. No. 690,706, May 27, 1976, abandoned.

[51] Int. Cl.$^2$ .......................... A61F 1/24; A41C 3/10
[52] U.S. Cl. .................. 3/36; 128/DIG. 21; 206/524.1; 206/524.6; 528/10
[58] Field of Search ............... 260/46.5 G, 46.5 UA; 3/36; 206/524.1, 524.6; 128/DIG. 21

[56] References Cited

U.S. PATENT DOCUMENTS

| | | | |
|---|---|---|---|
| 3,020,260 | 2/1962 | Nelson | 260/46.5 |
| 3,293,663 | 12/1966 | Cronin | 3/36 |
| 3,559,214 | 2/1971 | Pangman | 3/36 |
| 3,600,718 | 8/1971 | Boone | 3/36 |
| 3,665,520 | 5/1972 | Perras et al. | 3/36 |
| 3,681,787 | 8/1972 | Perras | 3/36 |
| 3,697,473 | 10/1972 | Polmanteer et al. | 260/46.5 UA |
| 3,852,832 | 12/1974 | McGhan et al. | 3/36 |
| 3,896,506 | 7/1975 | Hankin et al. | 3/36 |
| 3,911,503 | 10/1975 | Hankin | 3/36 |
| 3,934,274 | 1/1976 | Hartley, Jr. | 3/36 |
| 4,019,209 | 4/1977 | Spence | 3/36 |

*Primary Examiner*—Melvyn I. Marquis
*Attorney, Agent, or Firm*—Roger H. Borrousch

[57] ABSTRACT

A gel filled flexible article which is a container having silicone rubber walls of less than 0.0015 meter thick filled with a silicone gel such that the silicone gel contacts the silicone rubber wall, provides a low oiling article where the silicone rubber is based on an essentially polydimethylsiloxane gum and the gel is a crosslinked polydimethylsiloxane and has a penetration of 10 to 60 millimeters and produces a linear swell of the silicone rubber when said silicone rubber is encapsulated in the gel for 21 days at room temperature of less than 5 percent. The gel filled flexible articles are useful as external breast prostheses.

12 Claims, No Drawings

LOW OILING GEL FILLED FLEXIBLE ARTICLES AND GELS THEREFOR

This application is a continuation-in-part of application Ser. No. 690,706, filed May 27, 1976 and now abandoned.

BACKGROUND OF THE INVENTION

1. Field of the Invention

This invention relates to gel filled flexible articles and the gels therefor.

Description of the Prior Art

The combination of a silicone rubber container filled with a silicone gel is well known in the art. Such articles are known for use as surgically implantable human breast prostheses, as well as, external breast prostheses. Cronin in U.S. Pat. No. 3,293,663 describes a silicone rubber container filled with a soft silicone gel as an implantable breast prosthesis. Cronin describes a suitable gel as being one disclosed by Nelson in U.S. Pat. No. 3,020,260. The organosiloxane gel disclosed by Nelson is a reaction product of an intimate mixture of a triorganosiloxy endblocked polydiorganosiloxane having a viscosity of 100 to 10,000 cs. (approximately 0.1 to 10 pascal-seconds) at 25° C. and at least 0.174 molar precent of the units are RViSiO where Vi is vinyl and R is methyl or phenyl, and a liquid hydrogensiloxane of the formula

HRCH₃SiO(R₂SiO)ₙSiCH₃RH where R is methyl or phenyl and $n$ has a value to provide a viscosity of no more than 10,000 cs (approximately 10 pascal-seconds) at 25° C. and a platinum catalyst. These gels have at least one RViSiO unit for each silicon-bonded hydrogen atom. Cronin uses a gel where the ratio of atoms of silicon-bonded hydrogen per gram molecular weight of triorganosiloxy endblocked polydiorganosiloxane is adjusted to about 1.3 and where this gel preferably has a penetration from 30.0 to 20.0 mm. Cronin also suggests that the gel should be one which is inert toward the container. Other references to implantable prostheses include U.S. Pat. Nos. 3,559,214; 3,600,718; 3,665,520; 3,681,787; 3,852,832; and 3,934,274. External breast prostheses using silicone rubber containers and filled with silicone gel are described by Hankin et al. in U.S. Pat. No. 3,896,506 and Hankin in U.S. Pat. No. 3,911,503. These various patents describe methods of manufacture, designs and construction of both implantable and external breast prostheses. They also show the desirability of using silicone rubber containers with a silicone gel filling because of the low reactivity of the body toward the silicone materials and because the silicone materials may be easily cleaned and sterilized by steam or boiling water. Although these references show the desirability of the silicone materials, they do not discuss the problem encountered in using a silicone rubber as the container material and a silicone gel as the filling material. When a silicone gel is in contact with a silicone rubber there is a tendency for components of the gel to exude through the silicone rubber. If the gel filled silicone rubber container is an external breast prosthesis, the exudate will stain the wearer's clothing and be embarrassing. It is, therefore, desirable to reduce or eliminate the exudation, oiling or bleed of the gel components through the silicone rubber container. The prior art silicone gel filled silicone rubber containers have an undesirable amount of oiling or bleed because in order to obtain the desired penetration values for the gel with the appropriate natural simulated characteristics, large amounts of unreacted fluid were included in the gel network. This fluid would bleed through the silicone rubber container walls and thus be a problem as described above. A combination of materials has now been discovered which will provide an article with reduced oiling without departing from the desirable silicone materials.

SUMMARY OF THE INVENTION

An object of this invention is to provide a low oiling silicone gel filled silicone rubber container.

A silicone rubber comprising a gum of an essentially polydimethylsiloxane is used for container walls which are in contact with a silicone gel which is a crosslinked polydimethylsiloxane. Such articles have low oiling characteristics where the linear swell of the silicone rubber is less than 5 percent when the silicone rubber is encapsulated in the gel for 21 days at room temperature. These articles are useful as breast prostheses such as the external type, as well as, for other prostheses, pillows and pads.

One preferred silicone gel is prepared from dimethylvinylsiloxy endblocked polydimethylsiloxane which has an effective viscosity of 4.5 to 30 pascal-seconds (Pa·s) at 25° C.

DESCRIPTION OF THE INVENTION

This invention relates to a gel filled flexible article comprising a flexible container having at least a portion of the container wall composed of silicone rubber which is less than 0.0015 meters thick and said silicone rubber comprising a gum which is essentially polydimethylsiloxane, said container containing silicone gel which at least contacts the container wall composed of silicone rubber, said gel has a penetration of from 10 to 60 millimeters and produces a linear swell of the silicone rubber when said silicone rubber is encapsulated in the gel for 21 days at room temperature of less than 5 percent, and said gel comprising a crosslinked essentially polydimethylsiloxane.

The articles of this invention can be of any construction and can be made by any method inasmuch as the design, construction or method of manufacture constitutes no part of the present invention except that at least part of the wall portion which is made of silicone rubber be in contact with silicone gel. This combination is part of the invention because it is this relationship which will result in oiling or bleed.

Containers which have walls made of silicone rubber which is less than 0.0015 meter thick and which have silicone gel in contact with the silicone rubber wall will oil excessively unless the silicone rubber wall material has a linear swell of less than 5 percent when encapsulated in the silicone gel for 21 days at room temperature. Suitable combinations of wall material and gel can readily be determined by a simple swell test.

The container need not have all the walls made of silicone rubber as long as some silicone rubber wall is in contact with silicone gel. The silicone rubber is based on a gum which has been cured and which is essentially a polydimethylsiloxane. By essentially polydimethylsiloxane it is to be understood that the gum is composed of mostly dimethylsiloxane units but that other diorganosiloxane units can be present such as methylvinylsiloxane units, methylphenylsiloxane units, diphenylsiloxane units and 3,3,3-trifluoropropylsiloxane units, there being no more than 2 mol percent methylvinylsiloxane units and less than 25 mol percent of other diorganosiloxane units where the mol percentages are based on the total number of diorganosiloxane units in the gum. The gum can also contain minor amounts of monoorganosiloxane units and $SiO_2$ units which provide branching. The gums can be endblocked by conventional endblocking units such as triorganosiloxy units, such as dimethylvinylsiloxy units, trimethylsiloxy units or methylphenylvinylsiloxy units or hydroxyl groups. These gums are well known in the art and need not be discussed further.

The silicone rubber is well known and can contain fillers, such as reinforcing silica filler, processing aids, additives, pigments and can be vulcanized by conventional means, such as with organic peroxides, electromagnetic radiation, or by using a polysiloxane crosslinker containing silicon-bonded hydrogen atoms with a vinyl containing gum and a platinum catalyst. The proportions of these ingredients are well known in the art and those skilled in the silicone rubber art can readily adjust the ingredients and proportions to provide a silicone rubber which will suit their particular desires in physical properties.

The silicone gel suitable for this invention has a penetration of 10 to 60 millimeters and is a crosslinked polydimethylsiloxane. The gel must provide a linear swell of less than 5 percent to the silicone rubber when the silicone rubber is encapsulated in the gel for 21 days at room temperature. Preferably, the gel provides a linear swell of less than 5 percent to the silicone rubber when the silicone rubber is encapsulated in the gel for 60 days. The linear swell test is defined in more detail herein. The silicone gel is a crosslinked essentially polydimethylsiloxane. As stated above for the gum, other diorganosiloxane units, monoorganosiloxane units and $SiO_2$ units can be present in the gel in amounts similar to those stated for the gum.

One particular type of silicone gel suitable to provide less than 5 percent linear swell is based on a methylphenylvinylsiloxy endblocked polydimethylsiloxane which has an effective viscosity of 4.5 to 30 Pa·s at 25° C. By the phrase "an effective viscosity of 4.5 to 30 Pa·s at 25° C." is meant that the base polymer has a viscosity of 4.5 to 30 Pa·s at 25° C. or the base polymer in combination with suitable "in situ" chain extenders provides a gel which for all practical purposes is equivalent to a gel prepared from a base polymer having a viscosity of 4.5 to 30 Pa·s at 25° C. It has been found that this type of crosslinked polydimethylsiloxane gel in combination with the silicone rubber provides the desired linear swell.

The gel is to have a penetration of from 10 to 60 millimeters as determined by the method described in U.S. Pat. No. 3,293,663 which is hereby incorporated by reference to show the method of determining penetration values of gels. Preferably the penetration is from 25 to 45 millimeters, particularly for the breast prosthesis articles. Although the penetration values are not different from most gels used in these types of articles, it is pertinent to provide a range of penetration values for this invention in that the penetration values provide a means to determine a suitable degree of crosslinking wherein the base polymers have the viscosity range of 4.5 to 30 Pa·s at 25° C. The penetration values were obtained in prior art gels by using large amounts of unreacted fluid in the gel preparation such as trimethylsiloxy endblocked polydimethylsiloxane fluid. These types of fluids, because they remain unreacted, readily bleed through the silicone rubber container walls. Prior art gels which were examined and which did not contain the unreacted fluids were either too low in penetration values and rubber-like and/or would still bleed in undesirable amounts. It was found that only by providing a gel which provided less than 5 percent linear swell in the silicone rubber as stated above could the bleeding be reduced. One way of reducing the linear swell below 5 percent and likewise reducing the bleed through the silicone rubber container walls was by making a gel from a methylphenylvinylsiloxy endblocked polydimethylsiloxane which had a viscosity from 4.5 to 30 Pa·s at 25° C., and preferably from 6 to 12 Pa·s at 25° C. Although polymers of higher viscosity may also provide less than 5 percent linear swell, these polymers are difficult to work with, have a delicate stoichiometry and low penetration values.

The gels may be best prepared by mixing a methylphenylvinylsiloxy endblocked polydimethylsiloxane having a viscosity of 0.1 to 6 Pa·s at 25° C., preferably from 1.5 to 3 Pa·s at 25° C., a dimethylhydrogensiloxy endblocked polydimethylsiloxane having a viscosity of less than 0.5 Pa·s at 25° C. present in an amount sufficient to provide an effective viscosity for the methylphenylvinylsiloxy endblocked polydimethylsiloxane of 4.5 to 30 Pa·s at 25° C., a polymethylsiloxane having an average of at least three silicon-bonded hydrogen atoms per molecule where the polymethylsiloxane is present in an amount to provide a ratio of total silicon-bonded hydrogen atoms to vinyl radicals in the composition of from 0.2 to 0.8, preferably from 0.3 to 0.74 and a catalytic amount of a compatible platinum catalyst.

The methylphenylvinylsiloxy endblocked polydimethylsiloxanes are known in the art, as are the other ingredients. The general concept of chain extension for systems containing vinyl endblocked base polymers, silicon-bonded hydrogen polymers, silicon-bonded hydrogen endblocked chain extenders, polymethylsiloxanes containing at least three silicon-bonded hydrogen atoms and platinum catalysts are known for the preparation of silicone elastomers. These ingredients are further defined by Polmanteer et al. in U.S. Pat. No. 3,697,473 which is hereby incorporated by reference to further show these ingredients. Although Polmanteer et al. describe the various ingredients, they do not describe the preparation of gels as used herein.

The dimethylhydrogensiloxy endblocked polydimethylsiloxane is present in the composition to make the gel in amounts sufficient to provide the base polymer with a viscosity of 4.5 to 30 Pa·s at 25° C. Inasmuch as the silicon-bonded hydrogen atom content of this chain extender can vary considerably, as well as, the viscosity of the base polymer, any numerical value for the amount of chain extender is less precise than the above statement. To determine the amount of chain extender for a given base polymer viscosity and chain extender, silicon-bonded hydrogen atom content, one can mix the two in varying ratios with a small amount of platinum catalyst and then measure the viscosity after the material has reacted which takes only a few minutes. The desired combination can then be selected and used in the preparation of the gel. Preferably, the dimethylhydrogensiloxy endblocked polydimethylsiloxane has a silicon-bonded hydrogen atom content of 0.1 to 0.2 weight percent based on the weight of the chain extender and is present in amounts to provide an effective viscosity for the methylphenylvinylsiloxy endblocked polydimethylsiloxane of 6 to 12 Pa·s at 25° C.

After the amount of chain extender has been determined, the amount of crosslinker, the polymethylsiloxane, can then be found by using an amount sufficient to provide a ratio of total silicon-bonded hydrogen atoms to vinyl radicals of the base polymer in the composition of from 0.2 to 0.8, preferably from 0.3 to 0.74. The polymethylsiloxane can be any of a broad spectrum of siloxanes having silicon-bonded methyl radicals, where the units can be various combinations selected from dimethylsiloxane units, methylhydrogensiloxane units, trimethylsiloxy units, dimethylhydrogensiloxy units, monomethylsiloxane units, $SiO_2$ units and hydrogensiloxane units. The polymethylsiloxane has an average of at least three silicon-bonded hydrogen atoms per molecule and can contain 10 or more per molecule, preferably the polymethylsiloxane has an average of 4 to 8 silicon-bonded hydrogen atoms per molecule. The preferred polymethylsiloxanes are those which contain trimethylsiloxy units, dimethylsiloxane units and methylhydrogensiloxane units with a silicon-bonded hydrogen atom content of from 0.5 to 1.0 weight percent based on the weight of the polymethylsiloxane and a viscosity of less than 0.5 Pa·s at 25° C.

The platinum catalysts can be those which are described in Polmanteer et al. and which are compatible in the siloxane composition. The platinum catalysts are preferably the complexed platinum catalysts, such as the silicone platinum catalyst described by Willing in U.S. Pat. No. 3,419,593 which is hereby incorporated by reference to show a complexed platinum catalyst. The platinum catalyst is used in catalytic amounts such as greater than about 0.1 part by weight platinum per one million parts by weight of composition.

The gel can also contain pigments if it is desirable to provide a colored gel with a clear silicone rubber container or the silicone rubber can be pigmented to provide a colored article or both can be pigmented to provide a colored article. Color can also be produced by dyes.

The gel can be cured by allowing it to set at room temperature or it can be cured by heating it at a temperature of from 100° to 200° C. for from 10 to 60 minutes. Certainly other curing conditions may be found suitable and can be used so long as the desired gel characteristics are not destroyed. Inasmuch as, a combination of vinyl containing polymer, silicon-bonded hydrogen containing components and platinum catalyst will react at room temperature, they should not be stored in combination unless cure is desired. Preferably, it is desirable to mix the ingredients, except for the platinum catalyst and add the platinum catalyst just prior to the filling of the container which has a wall which is at least part silicone rubber of less than 0.0015 meter thick and then the gel composition is cured to a gel by heating.

The silicone gels which are suitable for this invention are those which provide less than a 5 percent linear swell for the silicone rubber when the silicone rubber is encapsulated in the gel for 21 days at room temperature, preferably less than 5 percent linear swell for the silicone rubber when the silicone rubber is encapsulated in the gel for 60 days at room temperature. The linear swell as used herein was determined by cutting a piece of silicone rubber of the appropriate thickness and about 2.8 by 5.0 centimeters. The sample length is measured to the nearest 0.01 centimeter. The sample is carefully cleaned by using isopropanol and allowed to dry before further testing. The test sample is then completely immersed in the gel to be tested and the resulting assembly is covered and allowed to stand for a designated time at room temperature. After the predetermined time, the silicone rubber test peice is removed from the gel and the length is measured to the nearest 0.01 centimeter. The percent linear swell is determined by subtracting the original length from the final length and multiplying by 100. If several time periods of immersion are desired, one can replace the test piece in the gel and continue the test for additional time.

The gel filled flexible articles of this invention were found to have reduced bleed or oiling and thus are more useful as an external breast prosthesis. This reduced bleeding characteristic was observed where the silicone rubber was based on an essentially polydimethylsiloxane gum and the gel in contact with this silicone rubber provided linear swell of less than 5 percent.

The bleed as shown in the examples was determined by lining a crystallization dish with aluminum foil, washing the aluminum foil with isopropanol and then drying for about 10 minutes in an oven at 100° C., cooling the dish to room temperature, weighing the dish, washing a gel filled flexible article with isopropanol, and then placing the article in the dish and storing it in a clean, dry place which is free of any possible dust contaimination or other possible causes for weight increases. After a predetermined time period, the dish containing the article is filled with isopropanol, the article is then moved in the isopropanol for two or three minutes and then the article is lifted from the dish allowing all the solvent to drip into the dish. The removed article is then washed thoroughly by spraying a stream of isopropanol over the article surface while allowing the wash to drip the dish. The rinsing is repeated three times. After all the isopropanol has dripped into the dish, the article is allowed to air dry and the dish containing the isopropanol solution is placed on a hot plate and heated gently to slowly evaporate some of the isopropanol. When a small amount of solution remains the dish is placed in a 100° C. oven for about 10 minutes to evaporate the remaining isopropanol. The dish is removed from the oven, allowed to cool to room temperature and then weighed. The amount of bleed is determined by subtracting the original weight from the final weight and the result is the amount of material which exuded from the article and is the amount of bleed.

The following examples are illustrative only and should not be construed as limiting the present invention which is properly delineated in the claims. All parts are parts by weight unless otherwise stated and all viscosities are at 25° C. unless otherwise stated.

Example 1

A. A silicone gel was prepared by mixing 97.5 parts of methylphenylvinylsiloxy endblocked polydimethylsiloxane having a viscosity of 0.00216 square meters per second ($m^2/s$) (hereinafter identified as Polymer A), 2.40 parts of dimethylhydrogensiloxy endblocked polydimethylsiloxane having a silicon-bonded hydrogen atom content of 0.159 percent by weight and sufficient to provide Polymer A with an effective viscosity of 0.0101 $m^2/s$ (about 10.1 Pa·s), 0.21 part of trimethylsiloxy endblocked polymethylsiloxane having 20 mol percent trimethylsiloxy units, 30 mol percent dimethylsiloxane units and 50 mol percent methylhydrogensiloxane units and having a silicon-bonded hydrogen atom content of 0.779 percent by weight and 0.1 part of a chloroplatinic acid catalyst complex with symmetrical divinyltetramethyldisiloxane containing about 0.65 weight percent platinum and prepared in accordance with the method defined in U.S. Pat. No. 3,419,593. The resulting mixture was heated for 20 minutes at 160° C. to cure the composition. The molecular weight of the methylphenylvinylsiloxy endblocked polydimethylsiloxane can be approximated by the formula in U.S. Pat. No. 3,020,260 which is hereby incorporated by reference to show the calculation having the viscosity known.

B. A silicone gel was prepared by mixing 98.2 parts of Polymer A, 1.70 part of dimethylhydrogensiloxy endblocked polydimethylsiloxane having a silicon-bonded hydrogen atom content of 0.159 percent by weight and sufficient to provide Polymer A with an effective viscosity of 0.0049 m$^2$/s (about 4.9 Pa·s), 0.27 part of the polymethylsiloxane described in A. above with a silicon-bonded hydrogen atom content of 0.779 percent by weight and 0.1 part of the platinum catalyst as defined in A. above. The resulting mixture was cured by heating at 160° C. for 20 minutes.

C. A silicone gel was prepared by mixing 97.62 parts of methylphenylvinylsiloxy endblocked polydimethylsiloxane having a viscosity of 0.00184 m$^2$/s (about 1.84 Pa·s), 2.10 part of dimethylhydrogensiloxy endblocked polydimethylsiloxane having a silicon-bonded hydrogen atom content of 0.159 percent by weight and sufficient to provide methylphenylvinylsiloxy endblocked polydimethylsiloxane an effective viscosity of 0.0046 m$^2$/s (about 4.6 Pa·s), 0.28 part by weight of the polymethylsiloxane, 0.28 part of the polymethylsiloxane defined in A. above having a silicon-bonded hydrogen atom content of 0.779 percent by weight and 0.04 part of the platinum catalyst as defined in A. above. The resulting mixture was cured by heating at 160° C. for 20 minutes.

D. A silicone gel was prepared by mixing 99.90 parts of methylphenylvinylsiloxy endblocked polydimethylsiloxane having a viscosity of 0.00912 m$^2$/s (about 9.12 Pa·s), 0.22 part of the polymethylsiloxane defined in A. above having a silicon-bonded hydrogen atom content of 0.779 percent by weight and 0.1 part of platinum catalyst as defined in A. above. The resulting mixture was cured by heating for 20 minutes at 160° C.

E. A silicone gel was prepared for comparative purposes by mixing 99.53 parts of Polymer A, 0.37 part of the polymethylsiloxane as defined in A. above having a silicon-bonded hydrogen atom content of 0.779 percent by weight and 0.1 part of platinum catalyst as defined in A. above. The resulting mixture was cured by heating 30 minutes at 150° C.

F. A silicone gel was prepared for comparative purposes by mixing 99.97 parts of trimethylsiloxy endblocked polydiorganosiloxane having dimethylsiloxane units and methylvinylsiloxane units having about 0.3 weight percent vinyl radical and having a viscosity of about 0.8 Pa·s (hereinafter identified as Polymer B) and 0.03 part of the platinum catalyst as defined in A. above. To 100 parts of the resulting mixture, 3.62 parts of polymethylsiloxane defined in A. above having a silicon-bonded hydrogen atom content of 0.159 percent by weight was added. The resulting mixture was cured by heating for 30 minutes at 150° C.

G. A silicone gel was prepared for comparative purposes by mixing 91.22 parts of Polymer B, 8.75 parts of a trimethylsiloxy endblocked polydimethylsiloxane having a small amount of monomethylsiloxane units and having a viscosity of 0.0001 m$^2$/s (about 0.1 Pa·s), and 0.03 part of platinum catalyst as defined in A. above. To 100 parts of the resulting mixture, 3.30 parts of the polymethylsiloxane having a silicon-bonded hydrogen atom content of 0.159 percent by weight was added. The resulting mixture was cured by heating at 150° C. for 30 minutes.

H. A silicone gel was prepared for comparative purposes by mixing 91.22 parts of Polymer B, 8.75 parts of trimethylsiloxy endblocked polydimethylsiloxane having a viscosity of 0.001 m$^2$/s (about 1.0 Pa·s) and 0.03 part of platinum catalyst as defined in A. above. To 100 parts of the resulting mixture, 3.30 parts of the polymethylsiloxane having a silicon-bonded hydrogen atom content of 0.159 percent by weight was added. The resulting mixture was cured by heating at 150° C. for 30 minutes.

I. A silicone gel was prepared by mixing 96.60 parts of Polymer A, 3.30 parts of dimethylhydrogensiloxy endblocked polydimethylsiloxane having a silicon-bonded hydrogen atom content of 0.159 percent by weight and sufficient to provide Polymer A with an effective viscosity of 0.023 m$^2$/s (about 23 Pa·s), 0.12 part of the polymethylsiloxane as defined in A. above having a silicon-bonded hydrogen atom content of 0.779 percent by weight and 0.1 part of the platinum catalyst as defined in A. above. The resulting mixture was cured by heating for 20 minutes at 160° C.

J. A silicone gel was prepared by mixing 97.46 parts of methylphenylvinylsiloxy endblocked polydimethylsiloxane having a viscosity of 0.001968 m$^2$/s (about 1.968 Pa·s), (hereinafter identified as Polymer C), 2.50 parts of dimethylhydrogensiloxy endblocked polydimethylsiloxane having a silicon-bonded hydrogen atom content of 0.172 percent by weight and sufficient to provide Polymer C with an effective viscosity of 0.0064 m$^2$/s (about 6.4 Pa·s) and 0.325 parts of the polymethylsiloxane defined in A. above having a silicon-bonded hydrogen atom content of 0.782 percent by weight. To 100 parts of the resulting mixture, 0.04 part of platinum catalyst as defined in A. above was added. The resulting mixture was cured by heating for 20 minutes at 160° C.

K. A silicone gel was prepared by mixing 97.49 parts of Polymer C, 2.51 parts of dimethylhydrogensiloxy endblocked polydimethylsiloxane having a silicon-bonded hydrogen atom content of 0.172 percent by weight and sufficient to provide Polymer C with an effective viscosity of 0.0064 m$^2$/s (about 6.4 Pa·s) and 0.29 part of the polymethylsiloxane defined in A. above having a silicon-bonded hydrogen atom content of 0.782 percent by weight. To 100 parts of the resulting mixture, 0.04 part of the platinum catalyst as defined in A. above was added. The resulting mixture was cured by heating at 160° C. for 20 minutes.

L. A silicone gel was prepared by mixing 97.50 parts of Polymer C, 2.51 parts of dimethylhydrogensiloxy endblocked polydimethylsiloxane having a silicon-bonded hydrogen atom content of 0.172 percent by weight and sufficient to provide Polymer C with an effective viscosity of 0.0064 m$^2$/s (about 6.4 Pa·s) and 0.28 part of the polymethylsiloxane having a silicon-bonded hydrogen atom content of 0.782 percent by weight. To 100 parts of the resulting mixture, 0.04 part of the platinum catalyst defined in A. above was added. The resulting mixture was cured by heating at 160° C. for 20 minutes.

M. A silicone gel was prepared by mixing 99.73 part of methylphenylvinylsiloxy endblocked polydimethylsiloxane having a viscosity of 0.0092 m²/s (about 9.2 Pa·s), 0.23 part of the polymethylsiloxane as defined in A. above having a silicon-bonded hydrogen atom content of 0.782 percent by weight and 0.04 part of the platinum catalyst defined in A. above. The resulting mixture was cured by heating for 20 minutes at 160° C.

The bleed was determined on the silicone gel filled rubber article by the test defined above. The articles were an external breast prosthesis, with a silicone gel as identified in Table I. The silicone rubber was a reinforced silica filled polydimethylsiloxane gum which was vulcanized with 2,4-dichlorobenzoyl peroxide. The silicone rubber container has part of the wall of about 0.0006 meter thick and the remaining part of the wall of about 0.0011 meter thick. The silicone rubber containers for each test were the same size and were filled with approximately equal amounts of gel composition. The containers were filled with gel composition as defined and then the containers were sealed and allowed to stand for about 20 minutes, any air pockets were removed by a hypodermic syringe and the hole made by the needle sealed after the air was removed. The deaired, gel filled container was then cured in an oven at the cure temperature and for the times indicated for each gel composition.

The penetration was determined on cured gel samples as defined herein and the linear swell was also done as defined herein using the same cured silicone rubber as used in making the containers. The results of the bleed test, the linear swell test and the penetration were as shown in Table I.

II and 0.04 part of the platinum catalyst as defined in Example 1, A. The resulting viscosity of the reacted mixtures were determined and were as shown in Table II.

Table II

| Run No. | Viscosity of Vinyl Polymer, m²/s | SiH Content, Weight Percent | Chain Extended Viscosity, m²/s |
|---|---|---|---|
| 1. | 0.00200 | 0.129 | 0.00464 |
| 2. | 0.00200 | 0.159 | 0.00556 |
| 3. | 0.00200 | 0.172 | 0.00596 |
| 4. | 0.00216 | 0.129 | 0.00648 |
| 5. | 0.00216 | 0.159 | 0.00760 |
| 6. | 0.00216 | 0.172 | 0.00912 |
| 7. | 0.00256 | 0.129 | 0.00824 |
| 8. | 0.00256 | 0.159 | 0.00984 |
| 9. | 0.00256 | 0.172 | 0.01216 |

That which is claimed is:

1. A gel filled flexible article comprising a flexible container having at least a portion of the container wall composed of silicone rubber which is less than 0.0015 meters thick and said silicone rubber comprising a gum which is essentially polydimethylsiloxane, said container containing silicone gel which at least contacts the container wall composed of silicone rubber, said gel has a penetration of from 10 to 60 millimeters and produces a linear swell of the silicone rubber when said silicone rubber is encapsulated in the gel for 21 days at room temperature of less than 5 percent, and said gel comprising a crosslinked essentially polydimethylsiloxane.

2. The gel filled flexible article in accordance with claim 1 in which all the container walls are silicone rubber.

3. The gel filled flexible article in accordance with claim 2 in which the crosslinked essentially polydimethylsiloxane is prepared from methylphenylvinylsiloxy endblocked polydimethylsiloxane which has an effective viscosity of 4.5 to 30 pascal-seconds at 25° C.

4. The gel filled flexible article in accordance with claim 3 in which the crosslinked essentially polydimethylsiloxane is a composition prepared by mixing a methylphenylvinylsiloxy endblocked polydimethylsiloxane having a viscosity of 0.1 to 6 pascal-seconds at 25° C., a sufficient amount of a dimethylhydrogensiloxy end- Table I

| Gel Composition | Penetration, mm | Bleed After | | Linear Swell, After | |
|---|---|---|---|---|---|
| | | 21 Days | 56 Days | 21 Days | 61 Days |
| A | 42.3 | 0.19 | 0.31 | 4.77 | 4.96 |
| B | 59.9 | 0.23 | 0.36 | 4.79 | 5.39 |
| C | 31.5 | 0.22 | 0.33 | — | — |
| D | 49.8 | 0.19 | 0.34 | 4.19 | 4.19 |
| E* | 46.3 | 0.26 | 0.46 | 6.92 | 7.97 |
| F* | 49.4 | 0.31 | 0.60 | 7.23 | 8.64 |
| G* | 33.6 | 0.51 | 0.88 | 9.45 | 9.45 |
| H* | 33.6 | 0.35 | 0.66 | 7.68 | 8.27 |
| I | — | — | — | 3.81 | 4.61 |
| J | 19.0 | 0.22 | 0.44 | — | — |
| K | 32.4 | 0.16 | — | — | — |
| L | 41.4 | 0.15 | — | — | — |
| M | 38.3 | 0.17 | — | — | — |

*For comparative purposes.

EXAMPLE 2

This example is presented to assist those in determining the manner to use the chain extension technique. In Table II compositions prepared by mixing 97.86 parts of methylphenylvinylsiloxy endblocked polydimethylsiloxane having a viscosity as shown in Table II as the vinyl polymer, 2.10 parts of dimethylhydrogensiloxy endblocked polydimethylsiloxane having a silicon-bonded hydrogen atom (SiH) content as shown in Table blocked polydimethylsiloxane having a viscosity of less than 0.5 pascal-seconds at 25° C. to provide an effective viscosity for the methylphenylvinylsiloxy end-blocked polydimethylsiloxane of from 4.5 to 30 pascal-seconds at 25° C., a polymethylsiloxane having an average of at least three silicon-bonded hydrogen atoms per molecule present in an amount to provide a ratio of total silicon-bonded hydrogen atoms to vinyl radicals in the composition of from 0.2 to 0.8 and a catalytic amount of a compatible platinum catalyst.

5. The gel filled flexible article in accordance with claim 4 in which the gel has a penetration of 25 to 45 millimeters and is a composition prepared by mixing a methylphenylvinylsiloxy endblocked polydimethylsiloxane having a viscosity of from 1.5 to 3 pascal-seconds at 25° C., a sufficient amount of a dimethylhydrogensiloxy endblocked polydimethylsiloxane having a silicon-bonded hydrogen atom content of from 0.1 to 0.2 weight percent based on the weight of the dimethylhydrogensiloxy endblocked polydimethylsiloxane to provide an effective viscosity for the methylphenylvinylsiloxy endblocked polydimethylsiloxane of from 6 to 12 pascal-seconds at 25° C., a polymethylsiloxane composed of trimethylsiloxy units, dimethylsiloxane units and methylhydrogensiloxane units and having a silicon-bonded hydrogen atom content of from 0.5 to 1.0 weight percent based on the weight of the polymethylsiloxane and having a viscosity of less than 0.5 pascal-seconds at 25° C. and a catalytic amount of a compatible platinum catalyst.

6. The gel filled flexible article in accordance with claim 5 in which the silicone rubber comprises a crosslinked, reinforcing silica filled polydimethylsiloxane gum.

7. The gel filled flexible article in accordance with claim 1 which is an external breast prosthesis.

8. The gel filled flexible article in accordance with claim 6 which is an external breast prosthesis.

9. The gel filled flexible article in accordance with claim 7 in which the silicone rubber contains pigments simulating skin color.

10. The gel filled flexible article in accordance with claim 8 in which the silicone rubber contains pigments simulating skin color.

11. A silicone gel comprising a crosslinked essentially polydimethylsiloxane having a penetration of from 20 to 60 millimeters being prepared by mixing a methylphenylvinylsiloxy endblocked polydimethylsiloxane having a viscosity of 0.1 to 6 pascal-seconds at 25° C., a sufficient amount of a dimethylhydrogensiloxy endblocked polydimethylsiloxane having a viscosity of less than 5 pascal-seconds at 25° C. to provide an effective viscosity for the methylphenylvinylsiloxy endblocked polydimethylsiloxane of from 4.5 to 30 pascal-seconds at 25° C., a polymethylsiloxane having an average of at least three silicon-bonded hydrogen atoms per molecule present in an amount to provide a ratio of silicon-bonded hydrogen atoms to vinyl radicals in the total composition of from 0.3 to 0.74 and a catalytic amount of a compatible platinum catalyst, and thereafter curing the composition to obtain a gel.

12. The silicone gel in accordance with claim 11 in which the gel has a penetration of 25 to 45 millimeters and is prepared by mixing a methylphenylvinylsiloxy endblocked polydimethylsiloxane having a visocisty of from 1.5 to 3 pascal-seconds at 25° C., a sufficient amount of a dimethylhydrogensiloxy endblocked polydimethylsiloxane having a silicon-bonded hydrogen atom content of from 0.1 to 0.2 weight percent based on the weight of the dimethylhydrogensiloxy endblocked polydimethylsiloxane to provide an effective viscosity for the methylphenylvinylsiloxy endblocked polydimethylsiloxane of from 6 to 12 pascal-seconds at 25° C., a polymethylsiloxane composed of trimethylsiloxy units, dimethylsiloxane units and methylhydrogensiloxane units and having a silicon-bonded hydrogen atom content of from 0.5 to 1.0 weight percent based on the weight of the polymethylsiloxane and having a viscosity of less than 0.5 pascal-seconds at 25° C., and a catalytic amount of a compatible platinum catalyst and thereafter curing the composition to obtain a gel.

* * * * *

UNITED STATES PATENT AND TRADEMARK OFFICE
CERTIFICATE OF CORRECTION

PATENT NO. : 4,100,627

DATED : July 18, 1978

INVENTOR(S) : Alfred P. Brill, III

It is certified that error appears in the above-identified patent and that said Letters Patent are hereby corrected as shown below:

Column 6, line 35: the phrase "to drip the dish" should read "to drip into the dish"

Signed and Sealed this

Twenty-fifth Day of September 1984

[SEAL]

Attest:

Attesting Officer

GERALD J. MOSSINGHOFF

Commissioner of Patents and Trademarks